United States Patent [19]

Kirsch

[11] Plant 4,881

[45] Aug. 24, 1982

[54] LILY NAMED LAURA

[75] Inventor: Ted T. Kirsch, Myrtle Point, Oreg.

[73] Assignee: Sun Valley Bulb Farms, Inc., Myrtle Point, Oreg.

[21] Appl. No.: 215,234

[22] Filed: Dec. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—C. W. Rummler

[57] ABSTRACT

A new and distinct variety of lily plant of the Parkmannis-type Oriental Hybrid particularly distinguished by its glossy, rosy pink, moderately spotted, white edged, upwardly and outwardly facing flowers which are borne in raceme arrangement on long, strong, upright pedicels, usually with one bud or flower on each pedicel, and by its dark green, relatively disease-resistant foliage.

2 Drawing Figures

BACKGROUND OF THE NEW PLANT

My new lily plant originated as a seedling of unknown parentage growing at my nursery in Arcata, Calif. Its relatively disease-resistant, brilliantly colored flowers and dark green, glossy foliage led me to select this new plant for asexual propagation and study with the result that I have found distinctive and advantageous characteristics in the new plant which make it a valuable addition to the field of commercial lily culture cut flower production. Propagation of this new lily through successive generations by means of scales and tissue culture at Arcata, Calif., has shown that its distinctive characteristics hold true from generation to generation and appear to be firmly fixed.

DESCRIPTION OF THE DRAWINGS

This new variety of lily plant is illustrated by the accompanying full color photographic drawing, which shows a full grown blooming plant in the upper view and a close-up of several blooms in the lower view, the color rendition being as nearly true as can be reasonably obtained by conventional photographic procedures.

DESCRIPTION OF THE NEW PLANT

The following is a detailed description of my new variety of lily plant as observed at Arcata, Calif., the observations having been made among field grown plants in the summer of 1980. The color designations are according to the R.H.S. Colour Chart published by The Royal Horticultural Society of London, England.

THE PLANT

Origin: Seedling.
Parentage: Unknown.
Classification: Oriental hybrid—Parkmannis.
Form: A single upright stem from each bulb.
Height: 3 to 5 feet at maturity.
Growth: Sturdy and upright with excellent strength.
Cane size: The stems grow from about ¼ inch in diameter at the base, with the plant at a height of 2 feet, to about ¾ inch base diameter when the plant is at a height of about 4 feet.
Foliage:
*Quantity.*—Abundant.
*Size of leaf at flower cluster.*—Two at the base of each pedicel about 5 inches long and 2½ inches wide and one on the pedicel approximately 1½ inches from the flower bud 4 inches long and 1 inch wide.
*Shape.*—Ovate with cuspidate apex.
*Texture.*—Leather.
*Aspect.*—Smooth.
*Ribs and veins.*—Distinct, longitudinal veins from base to tip.
Stem bulblet (underground):
*Occurrence.*—One to three on each healthy normal plant at digging time.
*Size.*—From ¼ inch to 1 inch in diameter.
*Color.*—White, with occasional pink shading at the tips.
Bulbs:
*Size.*—From about 6 inches to about 10 inches in circumference, depending on age.
*Color.*—White, with yellow and pink overtones. As the bulbs become larger and older, the overtones of yellow and pink become more and more prominent.

THE BUD

Form: Lanceolate, with acuminate apex.
Size: Averaging about 4 inches to 5 inches long and 1 inch to 1¼ inches in diameter.
Number: Usually one on each pedicel, with one to fifteen buds on a single stem according to culture and bulb size.
Opening rate: Normal; buds open successively from the lowermost bud to the top bud, which is the last to open.
Color: Whitish-pink at the tip of the bud, fading to raspberry pink at the base when the sepals are about to divide and petals begin to unfurl.
Surface texture: Rugose, leathery, with prominent veins.
Pedicel: Strong and generally upright, angled about 45° from the vertical.
*Color.*—Light green on bottom side, dark maroon on top, and generally glabrous.
*Length.*—About 2½ inches to 4 inches.

THE FLOWER

Blooming habit: Annually, blooming profusely in July.
Size of flower: Large; averaging about 7 to 8 inches in diameter.

Borne: From larger bulbs, the inflorescence has a raceme arrangement with each pedicel bearing one bud. The size of the bulb and its cultural care will determine the number of blooms and buds to be found on any given inflorescence. From large bulbs, this lily may have from four to eight blooms open at one time.

Shape: Generally flat, with uniformly spaced petals in star arrangement, the very tips of the petals curving backwardly.

Petalage: Normal; three sepals and three petals.

*Form.*—Oval, with cuspidate apex and sinuate edges, prominent nectariferous grooves and a center furrow bisecting each petal longitudinally.

*Size.*—About 5 inches long and 2 inches wide.

*Color.*—Upper side: upon opening, the midrib is Red Purple RHS 57B fading to RHS 63B for balance of petal with a $\frac{1}{8}$ to $\frac{1}{4}$ inch slightly frilled edge of White RHS 155D. The center inside half of the petal is moderately covered with dark maroon oblong spots. Under side: sepals are Red Purple RHS 66C. Petals are Red Purple RHS 65A and glabrous.

*Papillae.*—Present on petals and from 4 to 8 in number.

*Texture.*—Leathery.

*Aspect.*—Velvety.

Fragrance: Sweet.

Discoloration: The color darkens somewhat as the blossom matures.

Effect of weather: The flower generally not affected by wet weather, but flower ages as temperature rises.

Persistence: The petalage tends to hang on and dry.

Lasting quality:

*On the plant.*—Two to three weeks depending upon the size of the bulb and environmental temperature.

*As a cut flower.*—Ten days to two weeks.

REPRODUCTIVE ORGANS

Stamens:

*Anthers.*—Six in number, about $1\frac{3}{8}$ inches long, and in orderly arrangement around the pistil.

*Filaments.*—Length—$2\frac{3}{4}$ inches.

*Color.*—Rust.

Pistils:

*Number.*—One.

*Style.*—Length—about 3 inches. Color: light green at the base, darkening somewhat at the stigma.

*Stigma.*—Color: purple-gray.

*Ovary.*—Classified as a schizocarp. About 4 inches long and $1\frac{1}{2}$ inches in diameter, dehiscing into thirds and containing six rows of seeds of the usual shape for lilies.

I claim:

1. A new and distinct variety of Oriental Hybrid lily plant substantially as herein shown and described, characterized by its large, upwardly and outwardly facing flowers borne on strong stiff pedicels, by the substantially overall rosy pink coloring of the sepals and petals which are bordered by a frilly marginal band of white, and by the profuse production of flowers which have a long lasting quality whether on the plant or as cut flowers.

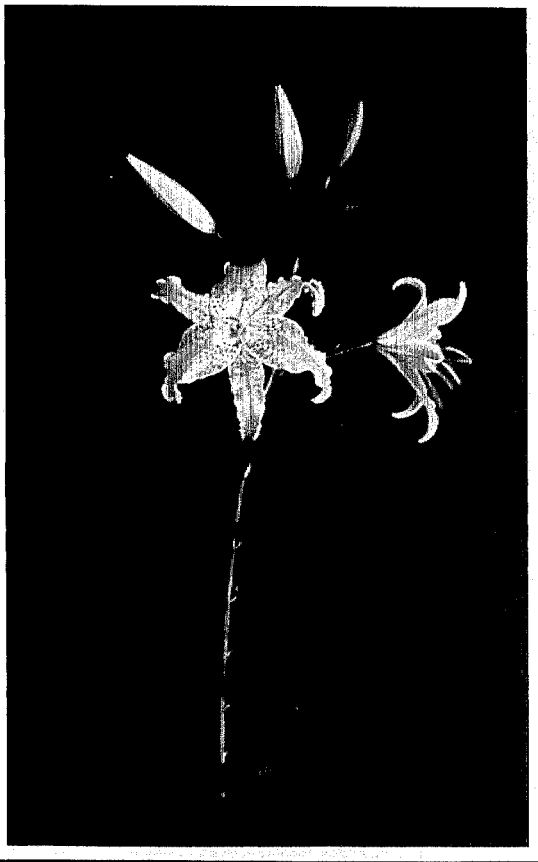
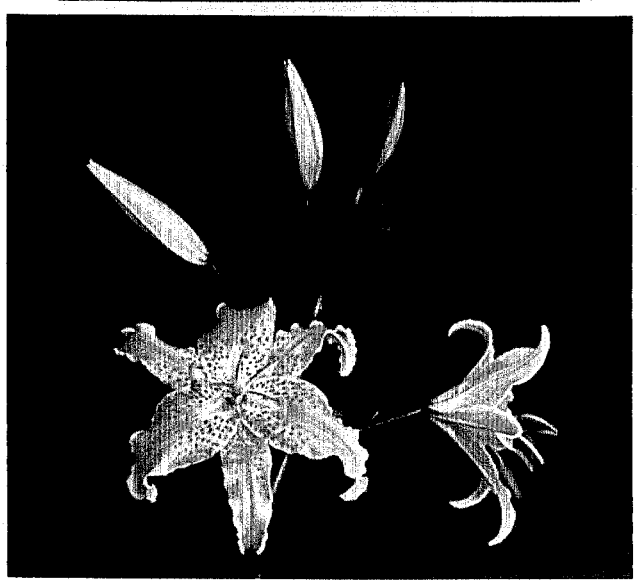

* * * * *